United States Patent
Tekiela et al.

(10) Patent No.: US 11,344,374 B2
(45) Date of Patent: May 31, 2022

(54) DETECTION OF UNINTENTIONAL MOVEMENT OF A USER INTERFACE DEVICE

(71) Applicant: Verily Life Sciences LLC, South San Francisco, CA (US)

(72) Inventors: Kamilla Tekiela, San Francisco, CA (US); Joëlle K. Barral, Mountain View, CA (US); Caitlin Donhowe, Mountain View, CA (US)

(73) Assignee: Verily Life Sciences LLC, South San Francisco, CA (US)

( * ) Notice: Subject to any disclaimer, the term of this patent is extended or adjusted under 35 U.S.C. 154(b) by 389 days.

(21) Appl. No.: 16/517,387

(22) Filed: Jul. 19, 2019

(65) Prior Publication Data

US 2020/0046439 A1 Feb. 13, 2020

Related U.S. Application Data

(60) Provisional application No. 62/718,169, filed on Aug. 13, 2018.

(51) Int. Cl.
*A61B 34/30* (2016.01)
*A61B 34/00* (2016.01)
(Continued)

(52) U.S. Cl.
CPC .............. *A61B 34/25* (2016.02); *A61B 34/30* (2016.02); *A61B 34/76* (2016.02); *B25J 9/161* (2013.01);
(Continued)

(58) Field of Classification Search
USPC ................................................ 700/245–264
See application file for complete search history.

(56) References Cited

U.S. PATENT DOCUMENTS 6,723,106 B1 4/2004 Charles et al.
8,073,528 B2 * 12/2011 Zhao ...................... B25J 13/089
700/245

(Continued)

FOREIGN PATENT DOCUMENTS

CN 101785704 A 7/2010
CN 201814653 U 5/2011
(Continued)

OTHER PUBLICATIONS

Bagalá, F., et al., "Evaluation of Accelerometer-Based Fall Detection Algorithms on Real-World Falls," PLOS One 7(5):e37062, May 2012, 9 pages.

(Continued)

*Primary Examiner* — Jonathan L Sample
(74) *Attorney, Agent, or Firm* — Christensen O'Connor Johnson Kindness PLLC

(57) ABSTRACT

A user interface system includes one or more controllers configured to move freely in three dimensions, where the one or more controllers include an inertial sensor coupled to measure movement of the one or more controllers, and output movement data including information about the movement. The user interface system further includes a processor coupled to receive the movement data, where the processor includes logic that, when executed by the processor, causes the user interface system to perform operations, including receiving the movement data with the processor, identifying an unintentional movement in the movement data with the processor, and outputting unintentional movement data that identifies the unintentional movement.

18 Claims, 5 Drawing Sheets

(51) Int. Cl.
*G06N 3/08* (2006.01)
*B25J 9/16* (2006.01)
*G06N 20/00* (2019.01)

(52) U.S. Cl.
CPC ............ *B25J 9/163* (2013.01); *B25J 9/1607* (2013.01); *G06N 3/08* (2013.01); *G06N 20/00* (2019.01)

(56) References Cited

U.S. PATENT DOCUMENTS

| | | | | |
|---|---|---|---|---|
| 8,918,211 | B2* | 12/2014 | Diolaiti | A61B 34/77 |
| | | | | 901/33 |
| 9,220,570 | B2* | 12/2015 | Kim | A61B 17/1285 |
| 9,463,571 | B2* | 10/2016 | Sinyavskiy | G06N 3/049 |
| 10,159,428 | B1* | 12/2018 | Shoeb | A61B 5/4082 |
| 2003/0013949 | A1 | 1/2003 | Moll et al. | |
| 2004/0243147 | A1* | 12/2004 | Lipow | A61B 34/74 |
| | | | | 606/130 |
| 2007/0238981 | A1* | 10/2007 | Zhu | A61B 34/20 |
| | | | | 600/424 |
| 2008/0292194 | A1* | 11/2008 | Schmidt | G06T 7/143 |
| | | | | 382/131 |
| 2011/0015649 | A1 | 1/2011 | Anvari et al. | |
| 2011/0306985 | A1 | 12/2011 | Inoue et al. | |
| 2013/0274596 | A1 | 10/2013 | Azizian et al. | |
| 2013/0338479 | A1* | 12/2013 | Pogue | A61B 5/7264 |
| | | | | 600/408 |
| 2014/0039517 | A1* | 2/2014 | Bowling | A61B 34/32 |
| | | | | 606/130 |
| 2014/0046128 | A1* | 2/2014 | Lee | A61B 34/30 |
| | | | | 600/102 |
| 2014/0094968 | A1* | 4/2014 | Taylor | B25J 13/006 |
| | | | | 700/257 |
| 2014/0184608 | A1* | 7/2014 | Robb | G06T 7/11 |
| | | | | 345/440 |
| 2014/0222023 | A1 | 8/2014 | Kim et al. | |
| 2014/0297130 | A1* | 10/2014 | Griffiths | G05D 1/0011 |
| | | | | 701/41 |
| 2015/0094736 | A1* | 4/2015 | Malackowski | A61B 5/4504 |
| | | | | 606/130 |
| 2015/0213652 | A1* | 7/2015 | Voigt | G06T 19/20 |
| | | | | 382/131 |
| 2015/0235360 | A1* | 8/2015 | Zheng | G06V 10/44 |
| | | | | 382/128 |
| 2016/0135729 | A1* | 5/2016 | Mestha | A61B 5/748 |
| | | | | 600/408 |
| 2017/0095295 | A1* | 4/2017 | Overmyer | A61B 18/1445 |
| 2017/0112580 | A1* | 4/2017 | Griffiths | A61B 34/30 |
| 2017/0340396 | A1* | 11/2017 | Romo | A61B 34/32 |
| 2018/0055577 | A1* | 3/2018 | Barral | A61B 34/20 |
| 2018/0065252 | A1* | 3/2018 | Tabandeh | B25J 9/1694 |
| 2018/0078319 | A1* | 3/2018 | Nobles | A47B 21/02 |
| 2018/0122506 | A1* | 5/2018 | Grantcharov | G16H 40/67 |
| 2018/0356895 | A1* | 12/2018 | Dailey | G06F 3/011 |
| 2019/0380801 | A1* | 12/2019 | Savall | A61B 34/37 |

FOREIGN PATENT DOCUMENTS

| | | | | |
|---|---|---|---|---|
| WO | | 98/33451 A1 | 8/1998 | |
| WO | | 2017/164818 A1 | 9/2017 | |
| WO | | WO-2018052796 A1 * | 3/2018 | ............ A61B 46/00 |

OTHER PUBLICATIONS

Gopal, P., et al., "Tremor Acquisition and Reduction for Robotic Surgical Applications," Proceedings of the 2013 International Conference on Advanced Electronic Systems (ICAES), Pilani, India, Sep. 21-23, 2013, pp. 310-312.

Morris, D., et al., "RecoFit: Using a Wearable Sensor to Find, Recognize, and Count Repetitive Exercises," Proceedings of the SIGCHI Conference on Human Factors in Computing Systems (CHI 2014), Apr. 26-May 1, 2014, Toronto, 10 pages.

Qu, W., et al., "Evaluation of a Low-Complexity Fall Detection Algorithm on Wearable Sensor Towards Falls and Fall-Alike Activities," Proceedings of the 2015 IEEE Signal Processing in Medicine and Biology Symposium (SPMB), Philadelphia, Dec. 12, 2015, 6 pages.

Veluvolu, K.C., and W.T. Ang, "Estimation of Physiological Tremor From Accelerometers for Real-Time Applications," Sensors 11:3020-3036, 2011.

Krupa et al., "Autonomous retrieval and positioning of surgical instruments in robotized laparoscopic surgery using visual servoing and laser pointers," Strasbourg I University, Louis Pasteur—LSIIT (UMR CNRS 7005), pp. 1-6.

Schulman et al., "A Case Study of Trajectory Transfer Through Non-Rigid Registration for a Simplified Suturing Scenario," Department of Electrical Engineering and Computer Sciences, University of California at Berkeley, CA, pp. 1-7.

Straub et al., "Autonomous High Precision Positioning of Surgical Instruments in Robot-Assisted Minimally Invasive Surgery under Visual Guidance," Mar. 2010, pp. 64-69, DOI: 10.1109/ICAS.2010.18.

International Search Report and Written Opinion dated Oct. 17, 2019 in corresponding International Patent Application No. PCT/US2019/045507, 12 pages.

* cited by examiner

DETECTION OF UNINTENTIONAL MOVEMENT OF A USER INTERFACE DEVICE

CROSS-REFERENCE TO RELATED APPLICATIONS

This application claims the benefit of U.S. Provisional Application No. 62/718,169, filed Aug. 13, 2018, which is hereby incorporated by reference in its entirety.

TECHNICAL FIELD

This disclosure relates generally to robotic systems.

BACKGROUND INFORMATION

Robotic or computer assisted surgery uses robotic systems to aid in surgical procedures. Robotic surgery was developed as a way to overcome limitations (e.g., spatial constraints associated with a surgeon's hands, inherent shakiness of human movements, and inconsistency in human work product, etc.) of pre-existing surgical procedures. In recent years, the field has advanced greatly to limit the size of incisions, and reduce patient recovery time.

In the case of surgery, robotically controlled instruments may replace traditional tools to perform surgical motions. Feedback-controlled motions may allow for smoother surgical steps than those performed by humans. For example, using a surgical robot for a step such as rib spreading may result in less damage to the patient's tissue than if the step were performed by a surgeon's hand. Additionally, surgical robots can reduce the amount of time a patient spends in recovery by facilitating smaller incisions.

Accidental drops or fumbles of user input devices or controllers lead to undesired behaviors. While these errors pose little risk for applications like gaming, a robot arm following the trajectory of a dropped controller during robotic surgery could be extremely dangerous for patients, and can additionally damage expensive hardware.

BRIEF DESCRIPTION OF THE DRAWINGS

Non-limiting and non-exhaustive embodiments of the invention are described with reference to the following figures, wherein like reference numerals refer to like parts throughout the various views unless otherwise specified. The drawings are not necessarily to scale, emphasis instead being placed upon illustrating the principles being described.

DETAILED DESCRIPTION

Figure 1A:
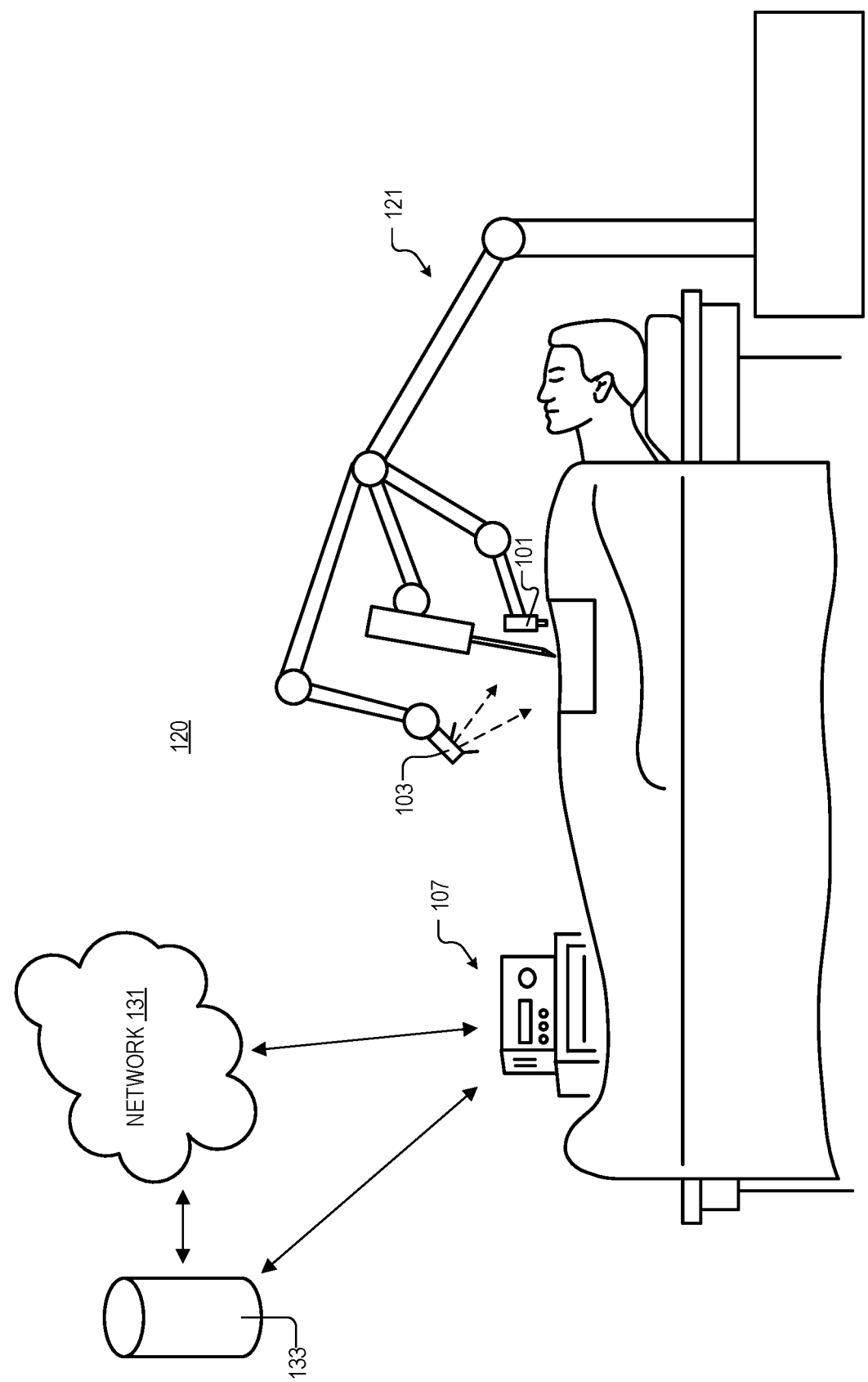
FIG. 1A illustrates a system for robotic surgery, in accordance with an embodiment of the disclosure.

Embodiments of a system and method for recognition of unintentional movement of a user interface device are described herein. In the following description, numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

User input devices (UIDs), also commonly referred to as "controllers", are pieces of hardware equipment that provide data and control signals to computers. When interacting in a 3D space, users hold an ungrounded controller in each hands and their movements are tracked through the use of accelerometers and other sensor technology. In the case of a surgical robotic platform, one or more controllers can be used to control robotic arms performing surgery.

As stated, accidental drops or fumbles of controllers lead to undesired behaviors. For safety concerns, it is vital to be able to distinguish between "intentional" and "unintentional" controller motions so that robot motion can be preemptively disabled when the user input cannot be trusted.

In a surgical platform, unintentional trajectories can take many forms. Heuristics can play an important role in identifying unintended motion, but it's difficult to be confident in the results in the absence of exhaustive data collection to fully explore the possible motion space.

The instant disclosure contemplates the application of machine learning to the development of a safe and robust method for detecting unintentional movement. A neural network (e.g., recurrent neural network (RNN) or a long-short term memory (LSTM) network or the like) can be used to predict whether or not a controller movement is intentional. The controller data (e.g., from an accelerometer, gyroscope, six degrees of freedom (6DOF) electromagnetic sensor, optical tracking sensor with LEDs, fiber optic position sensors, proximity sensors, and/or pressure sensor) may be summarized using a number of features.

The neural network can be trained with data recorded during surgical simulations, as well as in preclinical labs and using ongoing clinical data. Non-operational movements, including bobbling and drops of controllers, can also be recorded from the user. For each data point, data is labeled as either "intentional" or "unintentional". In some embodiments, data is characterized more granularly (e.g., with a confidence interval). Data can be labeled during the procedure, using bookmarking functionality on the robot (e.g., squeezing the controllers, or pressing a specific button on the UI, or performing one or more pedal combinations as a command). Capacitive sensors on the controllers can also be used as a supplementary "ground truth" for one type of unintentional behavior, drop detection (e.g., detecting when the fingers of the user are no longer on the controller). For training purposes, the data collection can be augmented by combining data sets or splicing drops into otherwise normal use (e.g., new training data may be created by inserting a drop from one data set into a different data set).

In one embodiment, anomaly detection is used for drop detection. While possibly not functional in the first moments of teleoperation, being able to detect an abrupt change in the quality of motion is a useful data point. That is, the neural network can learn a surgeon's typical motion in the first few milliseconds (e.g., 100 ms depending on the case, patient, surgeon, etc.) of a case, or use a preoperative calibration session, and if abnormal motion is detected after that, prevent it. Additionally, when the user is known, data recorded in previous cases, simulations, and preclinical labs can be used to inform what an unintentional motion is (e.g., in a connected system this data could be downloaded onto the robot currently in use).

Machine learning (ML) techniques are not necessarily replacements for heuristics. Because the risk of false negatives is so much more severe than that of false positives, "OR gating" multiple metrics together may provide the best guarantee of avoiding patient injury. A non-ML based, simple algorithm can threshold acceleration, rotational velocity, and jerk to detect drops. These thresholds can be tuned and improved based on the ML model. Some controller products may include capacitive sensors, which indicate whether a user is holding a controller (and therefore whether they have dropped a controller), which can also serve as an additional input.

A machine learning model or heuristic models can also output a confidence level rather than a binary unintentional/intentional result. This may be useful for risk mitigation when there is a lot of uncertainty about state of the system, and constant pausing due to possible drops would render the system unusable. When the controller is "probably not dropped" (as opposed to "certainly not dropped"), the system can limit tool velocities or scale commanded motions down so that damage from uncontrolled motion is limited. In some embodiments, the surgeon (or system, using computer vision) could also "tune" the acceptable motion depending on the step of the procedure or the type of procedure, and proceed with much more caution when close to critical structures. Similarly, if a step/procedure that requires abrupt or jerky motions (or a step that carries little or no risk of injury) is being performed, the system or user can dial back the motion suppression.

It is appreciated that while much of the disclosure herein is related to surgery, any product that involves tracking movement with an ungrounded input device could potentially use the technology disclosed herein. This could include a broad spectrum of devices, from gaming consoles, automated aircraft controls, to other surgical devices.

The following disclosure discusses the embodiments mentioned above, as well as other embodiments, as they relate to the figures.

FIG. 1A illustrates system 100 for robotic surgery, in accordance with an embodiment of the disclosure. System 100 includes surgical robot 121, camera 101, light source 103, processor 107, network 131, and storage 133. As shown, surgical robot 121 may be used to hold surgical instruments (e.g., each arm holds an instrument—or multiple instruments that are independently controlled—at the distal ends of the arm) and perform surgery, diagnose disease, take biopsies, or conduct any other procedure a doctor could perform. Surgical instruments may include scalpels, forceps, cameras (e.g., camera 101) or the like. While surgical robot 121 only has three arms, one skilled in the art will appreciate that surgical robot 121 is merely a cartoon illustration, and that surgical robot 121 can take any number of shapes depending on the type of surgery needed to be performed and other requirements. For example, two controllers may mean that two instruments on two arms are moving. But the disclosure here also contemplates using only one controller, three controllers, or four controllers (for example if two surgeons are performing the case simultaneously using one robot). It is appreciated that all arms could freeze if one controller is moved unintentionally, or only the arm corresponding to the unintentionally moved controller could freeze. Surgical robot 121 may be coupled to processing apparatus 107, network 131, and/or storage 133 either by wires or wirelessly. Furthermore, surgical robot 121 may be coupled (wirelessly or by wires) to a user interface (e.g., user interface system of FIG. 1B) to receive instructions from a surgeon or doctor, and send data (e.g., video) to a display. The user interface (UI), and user of the UI, may be located very close to the surgical robot 121 and patient (e.g., in the same room) or may be located many miles apart. Thus, surgical robot 121 may be used to perform surgery where a specialist is many miles away from the patient, and instructions from the surgeon are sent over the internet or secure network (e.g., network 131). In this embodiment, the window for anomaly detection might be related to the latency.

As shown, camera 101 is coupled to capture a video of a surgery performed by surgical robot 121. Processor 107 is coupled to surgical robot 121 to control the motion of the one or more arms, and camera 101 to receive the video from camera 101. Processor 107 includes logic that when executed by processor 107 causes processor 107 to perform a variety of operations. For example, in some embodiments that will be discussed in connection with FIG. 1B, the processor in the UI (or processor 107 in surgical robot 121 or a combination of the two) may register an unintentional movement (e.g., the surgeon dropping a surgical controller, jerking a controller, bobbling a controller, or shaking a controller). Unintentional movement data (e.g., data identifying or characterizing the unintentional movement) may be received by processor 107 of surgical robot 121, and in response to the unintentional movement data, surgical robot 121 may restrict the movement of its one or more arms. For example, surgical robot 121 may slow the motion of the one or more arms, entirely stop movement of the one or more arms, or pause the movement of the one or more arms until affirmative user input is received.

In one embodiment, camera 101 (e.g., including a CMOS image sensor or the like), pressure sensors (e.g., stress, strain, etc., disposed in the arms of robot 121), actuators (e.g., disposed in the arms of surgical robot 121 and including force measurement systems) and the like, are all used to control surgical robot 121 and ensure accurate motions and applications of pressure. Furthermore, these sensors may provide information to a processor (which may be included in surgical robot 121, processor 107, or other device) which uses a feedback loop to continually adjust the location, force, etc., applied by surgical robot 121. In some embodiments, sensors in the arms of surgical robot 121 may be used to determine the position of the arms relative to organs and other anatomical features. For example, surgical robot may store and record coordinates of the instruments at the end of the arms, and these coordinates may be used in conjunction with a video feed (or information derived from a soft tissue 3D simulator) to determine the location of the arms and anatomical features. It is appreciated that there are a number of different ways (e.g., from images, mechanically, time-of-flight laser systems, etc.) to calculate distances between components in system 100 and any of these may be used to determine surgical instrument location, in accordance with the teachings of the present disclosure.

Figure 1B:
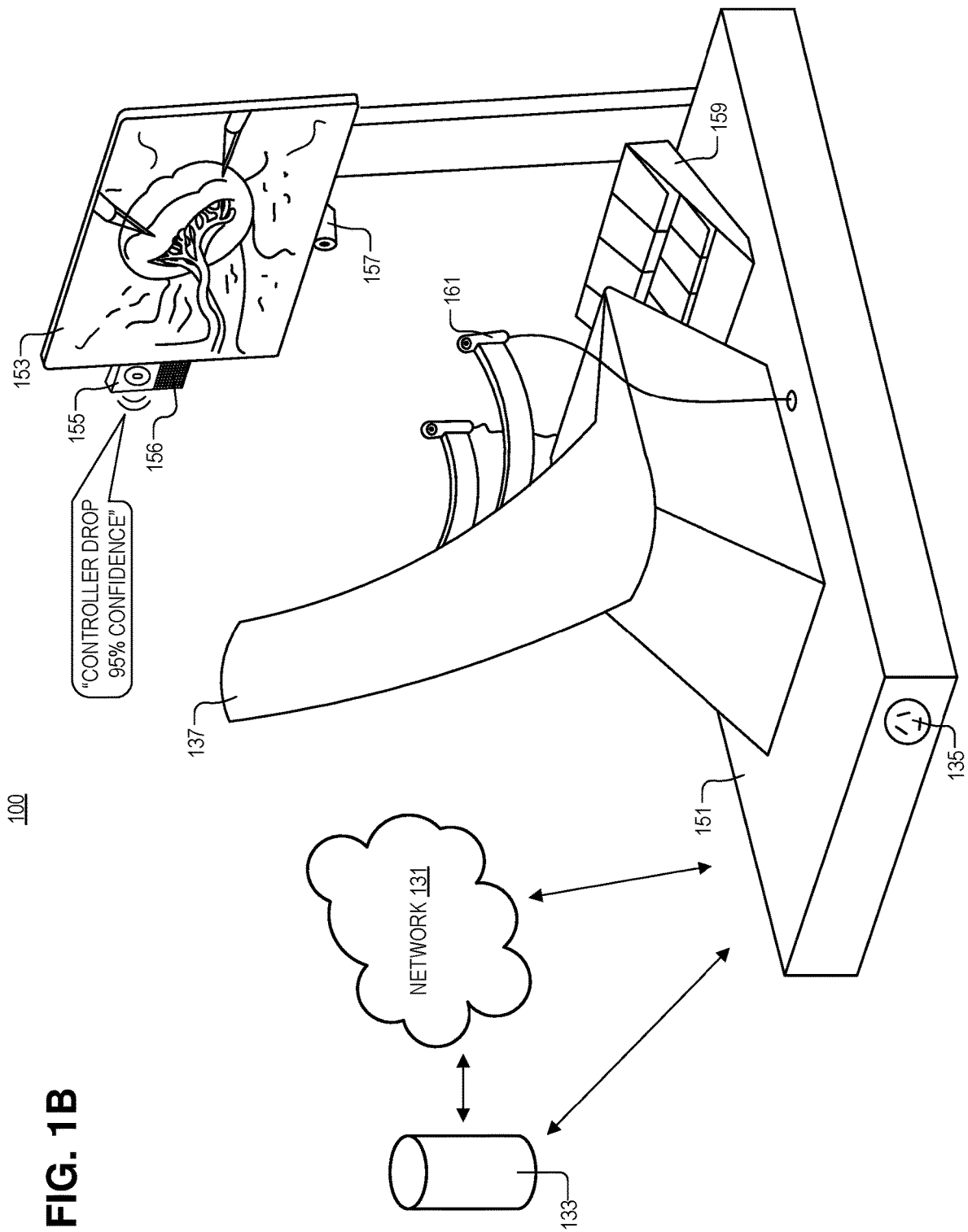
FIG. 1B illustrates a user interface system (for use with the system for robotic surgery depicted in FIG. 1A), in accordance with an embodiment of the disclosure.

FIG. 1B illustrates a user interface (UI) system 100 for use with the system for robotic surgery depicted in FIG. 1A, in accordance with an embodiment of the disclosure. Illustrated are network 131 (from FIG. 1A which may be used to communicate with surgical robot 121), storage 133 (also from FIG. 1A), power supply 135, command chair 137, processor 151, display 153, speaker 155, microphone 156, camera 157, control pedals 159, and one or more controllers 161.

Figure 2:
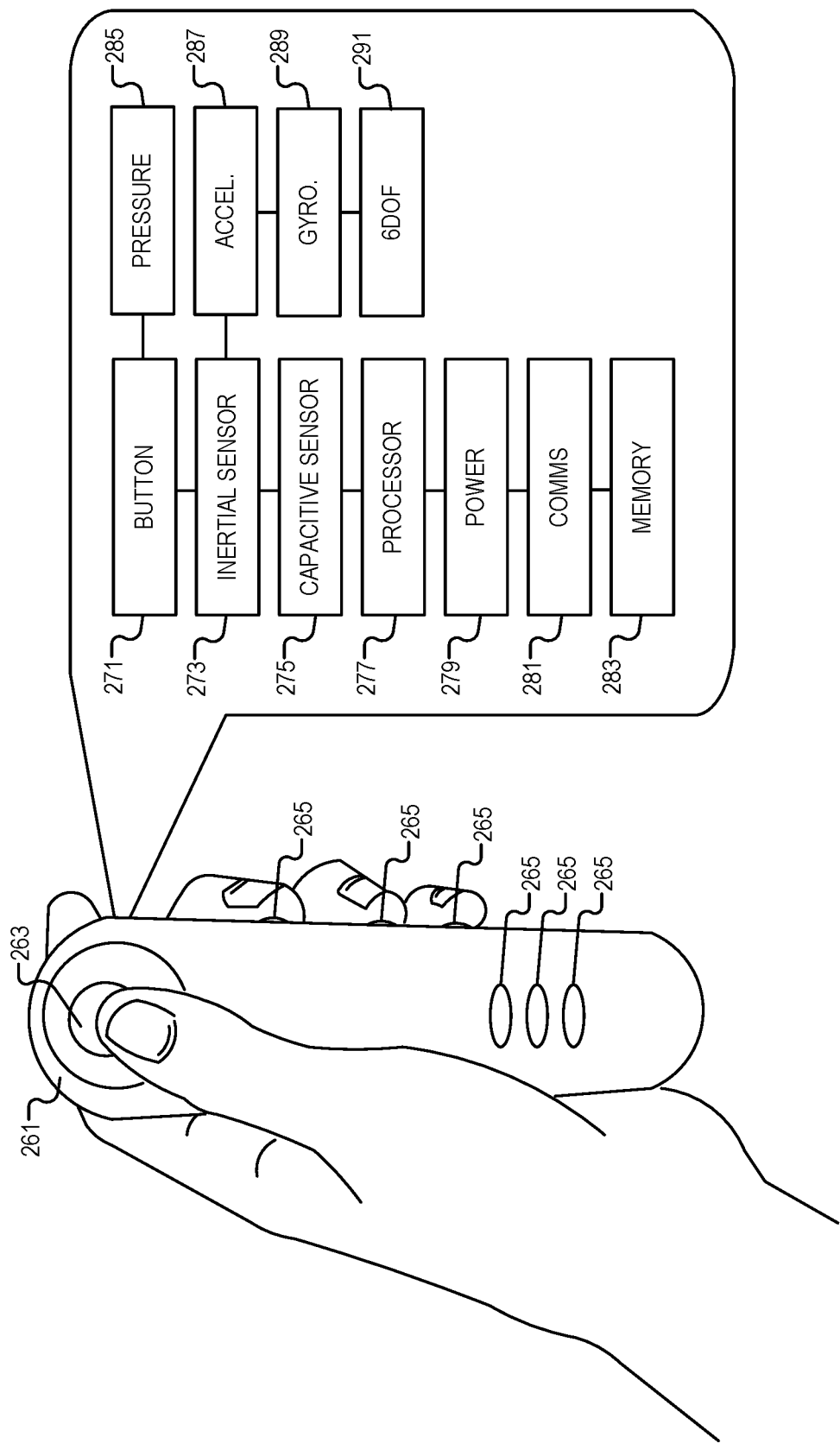
FIG. 2 illustrates a controller for the user interface system of FIG. 1B, in accordance with an embodiment of the disclosure.

As shown, one or more controllers 161 are attached to the arms of command chair 137 (e.g., by Velcro, magnets, a glove/pouch, being placed in a holder, or the like), and as will be shown in FIG. 2, controllers 161 are shaped to be hand held. The surgeon may sit in command chair 137 while performing surgery. As shown, much of the UI system 100 may be included in a single assembled device (e.g., chair 137, processor 151, display 153, which all may be supplied power though power supply 135). One or more controllers 161 may be detached from the arms of command chair 137, and once detached, controllers 161 are configured to move freely in three dimensions since, in the depicted example, they are only attached to a flexible cord. Put another way, unlike other surgical systems, there are no rigid hardware elements attached to the controllers 161 that limit their motion in one or more directions. Thus, when in use, one or more controllers 161 are physically unsupported (other than by the user's hand) when the user is operating user interface system 100. Accordingly, in some embodiments, controllers 161 have six degrees of freedom (e.g., controller 161 is free to move its position backward/forward, down/up, right/left (translation in three perpendicular directions) combined with rotational movement around three perpendicular axes, normal axis (yaw), lateral axis (pitch), and longitudinal axis (roll)). Thus, when UI system 100 is communicating with surgical robot 121 of FIG. 1A (e.g., through network 131 or a hardware connection), the surgeon has a free range of motion, which may enhance the surgeon's experience, reduce cost, and improve ergonomics.

As will be shown in FIG. 2, an inertial sensor is disposed within controllers 161 and is coupled to measure movement of controllers 161. The inertial sensor is coupled to output movement data (which includes information about the movement of controller 161). Processor 151 (e.g., contained within the housing depicted) is coupled to receive the movement data from controllers 161. It is appreciated that processor 151 may be local like the system depicted, or be part of a distributed system in network 131, or the like. Processor 151 may include a plurality of task specific processing elements (e.g., graphics cards to run machine learning algorithms) or general purpose processing units. In the depicted example, processor 151 includes logic that, when executed by processor 151, causes UI system 100 to perform operations, such as receiving the movement data with processor 151, identifying an unintentional movement in the movement data with processor 151, and outputting (e.g., to network 131 or storage 133) unintentional movement data. Processor 151 may send the unintentional movement data to surgical robot 121 in FIG. 1A (and/or its associated processor 107). And as discussed above, in response to the unintentional movement data, the surgical robot restricts the movement of the one or more arms. It is appreciated that UI system 100 also sends data about intentional movement of controllers 161 to move the arms of surgical robot 121.

In the depicted example, processor 151 may be running a machine learning algorithm (see e.g., FIG. 3) disposed in logic (e.g., software, hardware, or a combination thereof), which is used to identify an unintentional movement (e.g., the machine learning algorithm is trained to recognize when one of the sensors in the controller outputs data that may be characteristic of an unintended motion). In some embodiments, the machine learning algorithm includes at least one of recurrent neural network (RNN) or a long-short term memory (LSTM) network. In the depicted example, the machine learning algorithm is used to output a confidence interval that the unintentional movement occurred (e.g., in the depicted embodiment by having the speaker 155 state "controller drop 95% confidence" which may be heard by the user of the system). The confidence interval may be used to determine the amount of "slowing" or "motion scaling" of the robot arms. Additionally, the confidence interval might be used in combination with information about the surgeon (e.g., level of expertise), the procedure, the specifics of the current anatomy and location of the instruments, in order effectively reduce or eliminate unintentional motion.

In some examples, the machine learning algorithm may be used in conjunction with one or more thresholds, direct sensing of surgical instrument contact, anomaly detection, or heuristic methods to identify the unintentional movement. This is because thresholding or other methods may provide a less processor-intensive way to identify unintentional movement. For example, if an accelerometer in controller 161 registers the controller exceeding a velocity or acceleration (e.g., a threshold velocity or acceleration) that is greater than what is expected while the controller is held in a human hand, UI system 100 may register an unintentional movement (e.g., a dropped controller) without having to employ the more processor-intensive machine learning algorithms. Similarly, in some embodiments, controller 161 may include one or more buttons or a capacitive sensing system coupled to sense tactile input from a user, and output tactile data including information about the tactile input. Thus, if the tactile sensors in the controller register that the controller is not in contact with a human hand (e.g., a threshold condition) when a movement occurs, the system may register an unintentional movement. However, in some embodiments, input from the tactile sensor system and inertial sensor system may be used by the machine learning algorithm to detect unintentional movement.

In some embodiments, other inputs may be used by the machine learning algorithm to identify unintentional movement. In the depicted example, the system includes camera 157 which observes the surgeon. The video data output from camera 157 may be used by processor 151 to determine if an unintentional movement occurred. For example the video data may be analyzed by the machine learning algorithm to visually identify if the user bobbled, dropped, bumped, or shook controller 161. The machine learning algorithm could then output unintentional movement data (e.g., flag the movement data output from controller 161 as unintentional). In some embodiments, video data may be received from camera 101 in FIG. 1A, and actuator data may be received from robot 121 in FIG. 1A. The UI system 100 depicted here may analyze this data to identify if a movement was unintentional (e.g., if the tool/arm movement would cause a tool to hurt the patient or damage the tool). In one embodiment, the system may determine if a movement was unintentional by having the system "machine learn" the surgeon's tendencies (e.g., how fast/slow the surgeon typically moves, the surgeon's motion patterns, etc.), and restrict motion of the robot if the discrepancy between controller motion and predicted controller motion (based off of the surgeon's typical tendencies) is too high. Similarly, UI system 100 includes microphone 156, coupled to processor 151, which may listen to the surgeon/control room as the surgeon is performing surgery. The machine learning algorithm may be used to examine sound data output from microphone 156 to identify when an unintentional movement occurred. For example, when controller 161 is dropped the sound of controller 161 hitting the floor may be identifiable. Similarly, pedals 159 may be used to control the robot. Processor 151 may analyze input from pedals 159 to determine an unintentional movement. Both thresholding and the machine learning algorithm(s) may be used to identify unintentional movement data output from the pedals (e.g., unintentional pedal press). Combinations of the various algorithms employed could take into account data from all surgeons and/or all procedures, or only some of them.

In some embodiments, "OR gating" some or all of the various inputs described above (e.g., heuristics, thresholds, machine-identified unintentional movements, or the like) may be used to avoid false negatives. For example, if multiple of the sensor systems described above (or other sensor systems not described) register an unintentional movement, UI system 100 has high confidence that an unintentional movement occurred, and the system will arrest movement of the surgical robot accordingly. "OR gating" could only be applied in most critical situations or in all surgical situations.

FIG. 2 illustrates controller 261 for the user interface system of FIG. 1B, in accordance with an embodiment of the disclosure. In the depicted example, the controller 161 is physically unsupported (e.g., not held up by hardware) when the user is operating the user interface system. However, in other embodiments, controller 261 may be semi supported in some directions (e.g., a controller that has force feedback for position but not orientation). Controller 261 is shaped to be hand held (or hand worn, e.g., a Velcro strap behind the hand, which straps controller 261 to the hand), and in the depicted embodiment, controller 261 is wireless. Controller 261 includes joystick 263 (one example of a button), a plurality of press buttons 265, internal buttons 271 (including a pressure sensor 285, or the like), an inertial sensor 273 (including one or more of an accelerometer 287, a gyroscope 289, a six-degrees of freedom magnetic sensor system 291, or the like), a capacitive sensor system 275, an internal processor 277, a power source 279, communication logic 281, and memory 283. One of skill in the art will appreciate that controller 261 is just one illustration of a controller that may be used to control a surgical robot, and that other controller shapes, internal/external hardware, and software, may be used in accordance with the teachings of the present disclosure.

In the depicted example, the user may use the joystick 263 and the variety of buttons 265 to control the robot. By rotating controller 261, robot arms may rotate, move forward, backward, side to side, or the like. As shown, buttons 265 are disposed on the side of controller 261 under each of the user's fingers. Buttons are also placed on the top of controller 261 which may be used to perform specific commands (e.g., adjust display brightness, switch surgical instruments, etc.). In this embodiment, data from when the surgeon is performing teleoperation might be treated differently from data when the surgeon is using the various apps.

Within controller 261 may be some or all of the electronic components depicted. In some embodiments, several buttons may be substantially disposed on the interior of controller 261. For example, the sides of the controller 261 may be coupled to pressure sensors 285 (e.g., strain gauge, piezoelectric sensor, or the like) to feel when a user is gripping controller 273. In some embodiments, identifying unintentional movement includes analyzing the tactile data, output from one or more buttons 265, with the processor (e.g., processor 107 in FIG. 1A, processor 151 in FIG. 1B, or processor 277 in FIG. 2). Similarly, processor 277 may be coupled to capacitive sensors 275 on the surface of controller 261 (e.g., similar to the capacitive sensing of a touch screen) to determine if/how a user is holding controller 261 (e.g., determining placement of fingers on controller 261, if controller 261 is fully in hand, if controller 261 has been dropped, etc.). In some embodiments, continuous data (e.g., number of contact points, area of controller contacted, or amount of pressure) rather than bimodal (e.g., held not held) may be employed to determine control. For example, if the system is looking at points of contact, and there's only one point of contact, then controller 261 is unlikely to be under the surgeon's control. Similarly, if the surgeon is holding controller 261 at two points and then controller 261 registers five points of contact, there's a good chance it's been fumbled. Power source 279 (e.g., battery, charging circuitry, and the like) may be disposed in controller 261 to supply power to processor 277 (e.g., microcontroller, general purpose processor, or the like), communication logic 281 (e.g., RFID, Bluetooth, WiFi, or the like), and memory 283 (e.g., RAM, ROM, or the like). Processor 277 may process the inputs received from the various sensors in controller 261 to generate movement data which is sent to the processor in a UI system (e.g., processor 151 in FIG. 1B) via communication logic 281.

As depicted, the inertial sensor 273 may include one or more of an accelerometer 287, a gyroscope 289, a six-degrees of freedom magnetic sensor system 291, or the like, which are used to capture data about user movement. One of skill in the art will appreciate that there are any number of sensor systems (other than the ones depicted here) that can be used to capture user movement of controller 261. Any of these systems may be employed in accordance with the teachings of the present disclosure.

Figure 3:
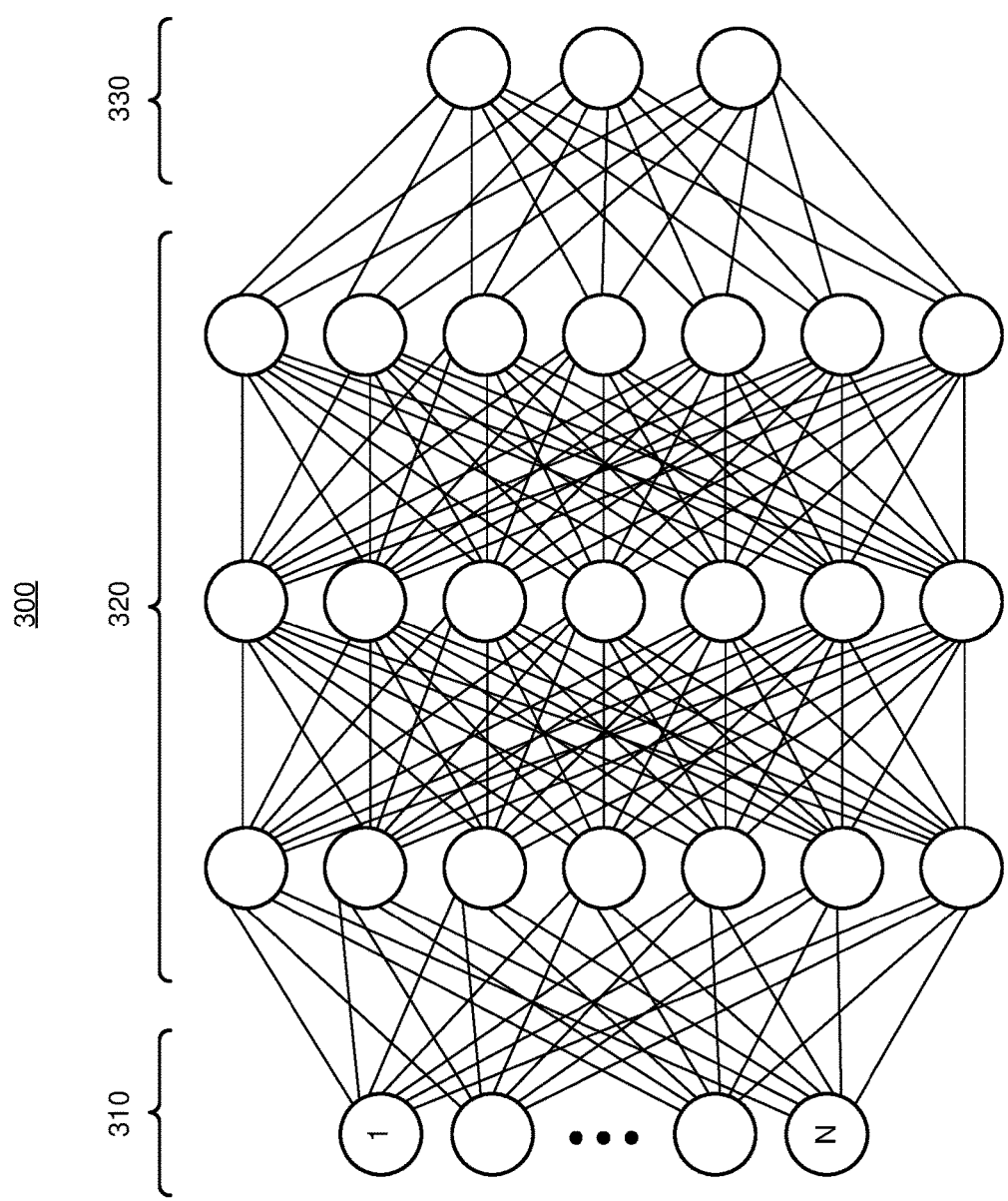
FIG. 3 is a graphical depiction of algorithms that may run on the user interface system of FIG. 1B, in accordance with an embodiment of the disclosure.

FIG. 3 is a graphical depiction of machine learning algorithms 300 that may run on the user interface system of FIG. 1B, in accordance with an embodiment of the disclosure. Machine learning algorithm 300 includes an input layer 310, an output layer 330, and multiple hidden layers 320 disposed between the input layer 310 and the output layer 330. The number of nodes in input layer 310 may be dependent on the inputs (e.g., from the various controllers, buttons, cameras, and microphones, depicted elsewhere), and output layer 330 may provide the assessment of the unintentional action. In some embodiments, the number of input nodes is related to the number of various inputs and their particular resolution (e.g., resolution of capacitive sensing elements on the surface of the controller). It is appreciated that multiple machine learning algorithms like the one depicted may be running (and trained) separately for each input (e.g., one algorithm for sensor input, one algorithm for video input, etc.). The weight distribution for the connections between nodes is not illustrated, but it is appreciated that the specific values are highly dependent on the training or pre-training method, the number of training iterations (e.g., number of training samples) performed, to name a few.

The type of neural network utilized for the machine learning algorithm 300 is highly configurable and dependent on the inputs and the data being analyzed. Thus, in some embodiments, the machine learning model 300 may utilize radial basis function neural network, a recurrent neural network, long-short term memory network, a convolution neural network, a modular neural network, or other types of neural networks. As described above, machine learning algorithm 300 may be used in conjunction (e.g., at the same time or in some sequential order) with other algorithms to identify the unintentional movement, in accordance with the teachings of the present disclosure.

Figure 4:
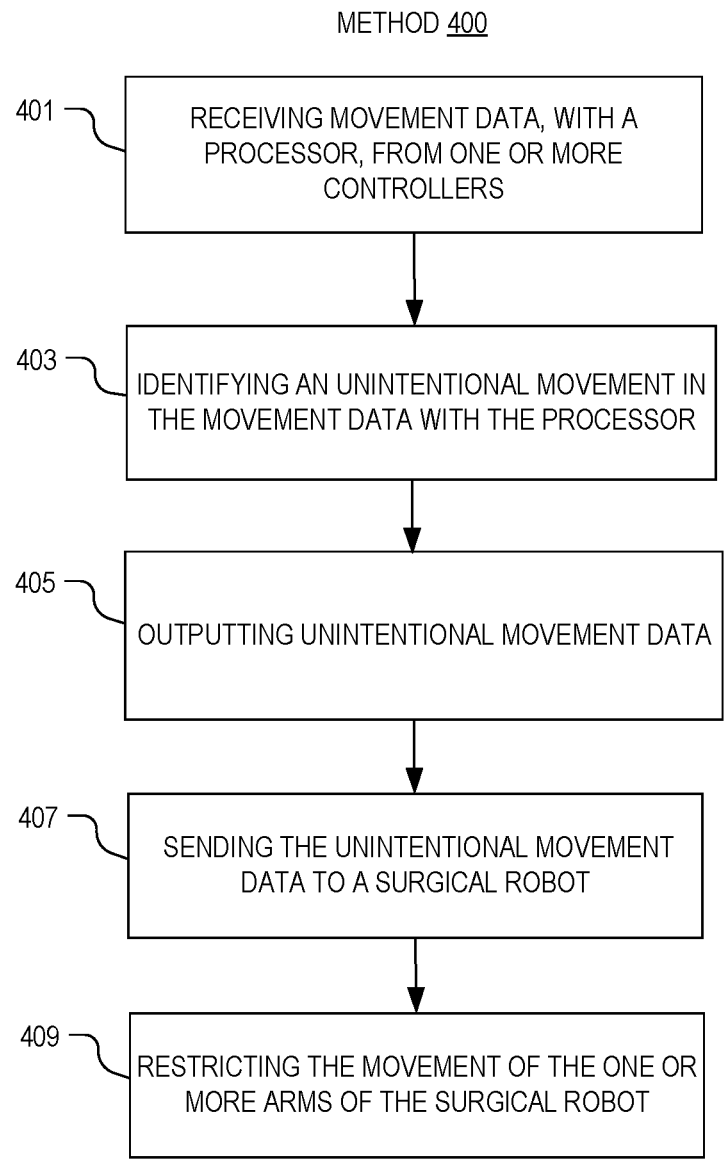
FIG. 4 illustrates a method of interacting with a robot, in accordance with an embodiment of the disclosure.

FIG. 4 illustrates a method 400 of interacting with a robot, in accordance with an embodiment of the disclosure. One of ordinary skill in the art having the benefit of the present disclosure will appreciate that the order of blocks (401-409) in method 400 may occur in any order or even in parallel. Moreover, blocks may be added to, or removed from, method 400 in accordance with the teachings of the present disclosure.

Block 401 shows receiving movement data, with a processor, from one or more controllers, where the controllers are configured to move freely in three dimensions (e.g., the controllers are not coupled to hardware that restricts their motion). The one or more controllers may include an inertial sensor to measure movement of the one or more controllers, and output movement data (e.g., location information, rotational information, acceleration, velocity, etc.). In one embodiment, the movement data includes information about the six degrees of freedom of the one or more controllers. In some embodiments, additional sensors could be attached to the surgeon (e.g., a watch, or a wrist patch) providing data of the motion of the hand (or monitoring neural signals) that can be correlated with the controller data to improve the detection Block 403 illustrates identifying an unintentional movement (e.g., a dropped controller, a jerked controller, a bobbled controller, or a shaken controller) in the movement data with the processor. It is appreciated that unintentional movement can include any action that causes the controller to move in a way that the surgeon did not desire. In some embodiments, the processor includes a machine learning algorithm disposed in logic, and the machine learning algorithm (e.g., a RNN or LSTM network) is used to identify the unintentional movement from the movement data.

In some embodiments, tactile data (e.g., output from at least one of a button, a pressure sensor, or a capacitive sensor) is also received from the controller, and the tactile data is indicative of a user touching the controller. In some embodiments, the unintentional movement is identified at least in part using the tactile data (e.g., by using the machine learning algorithm to look at the tactile data or the like). In one embodiment, the machine learning algorithm is used in conjunction with one or more present thresholds to identify the unintentional movement.

Block 405 describes outputting unintentional movement data, where the unintentional movement data includes information about the unintentional movement. The unintentional movement data may be output from the processor/memory to a bus or to a network.

Block 407 shows sending the unintentional movement data to a surgical robot including one or more arms. Thus, the surgical robot may revive the unintentional movement data from the bus or network. In some embodiments, the unintentional movement data may include flagging certain parts of movement data from a controller as "unintentional".

Block 409 illustrates, in response to the unintentional movement data, restricting the movement of the one or more arms of the surgical robot. In some embodiments, after the surgical robot receives data labeled as "unintentional" the surgical robot may stop moving its arms, may slow down the movement of its arms, may motion scale the arms or may temporarily freeze moment of its arms. The robot may then seek user input before it proceeds with the motion, or may request a corrected trajectory. In some embodiments, the robot could cache the motion in case it was intended and perform it after a confirmation input from the surgeon.

The processes explained above are described in terms of computer software and hardware. The techniques described may constitute machine-executable instructions embodied within a tangible or non-transitory machine (e.g., computer) readable storage medium, that when executed by a machine will cause the machine to perform the operations described. Additionally, the processes may be embodied within hardware, such as an application specific integrated circuit ("ASIC") or otherwise. Processes may also occur locally or across distributed systems (e.g., multiple servers, processors, and memory). Machine learning algorithm architectures may be implemented in software or hardware.

A tangible non-transitory machine-readable storage medium includes any mechanism that provides (i.e., stores) information in a form accessible by a machine (e.g., a computer, network device, personal digital assistant, manufacturing tool, any device with a set of one or more processors, etc.). For example, a machine-readable storage medium includes recordable/non-recordable media (e.g., read only memory (ROM), random access memory (RAM), magnetic disk storage media, optical storage media, flash memory devices, etc.).

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. A user interface system, comprising:
one or more controllers configured to move freely in three dimensions, wherein the one or more controllers include an inertial sensor coupled to measure controller movement of the one or more controllers, and output movement data including information about the controller movement; and
a processor coupled to receive the movement data from the one or more controllers, wherein the processor includes logic that, when executed by the processor, causes the user interface system to perform operations, including:
receiving the movement data with the processor;
identifying an unintentional movement in the movement data with the processor;
outputting unintentional movement data that identifies the unintentional movement; and
sending the unintentional movement data to a robotic surgery system to enable the robotic surgery system to restrict robotic movement in response to receiving the unintentional movement data.

2. The user interface system of claim 1, further comprising:
sending the unintentional movement data along with the movement data to the robotic surgery system.

3. The user interface system of claim 1, wherein the unintentional movement includes at least one of a dropped controller, a jerked controller, a bobbled controller, or a shaken controller.

4. The user interface system of claim 1, further comprising:
a tactile interface disposed in the one or more controllers and coupled to sense tactile input from a user of the user interface system and output tactile data including information about the tactile input, and wherein identifying the unintentional movement includes analyzing the tactile data, output from the tactile interface, with the processor.

5. The user interface system of claim 4, wherein the tactile interface includes at least one of a button, a pressure sensor, or a capacitive sensor.

6. The user interface system of claim 1, further comprising a machine learning algorithm disposed in logic, and wherein identifying an unintentional movement includes using the machine learning algorithm.

7. The user interface system of claim 6, wherein the machine learning algorithm includes at least one of recurrent neural network (RNN) or a long-short term memory (LSTM) network.

8. The user interface of claim 6, wherein the machine learning algorithm is used in conjunction with one or more heuristics to identify the unintentional movement.

9. The user interface of claim 1, wherein the processor further includes logic that, when executed by the processor, causes the user interface system to perform operations, including:
outputting, in the unintentional movement data, a confidence interval that the unintentional movement occurred.

10. The user interface system of claim 1, wherein the one or more controllers are physically unsupported when the user is operating the user interface system, and wherein the one or more controllers are shaped to be hand held or hand worn.

11. The user interface system of claim 10, wherein the one or more controllers have six degrees of freedom.

12. A method of interacting with a robot, comprising:
receiving movement data, with a processor, from one or more controllers configured to move freely in three dimensions, wherein the one or more controllers include an inertial sensor disposed within the one or more controllers to measure controller movements of the one or more controllers, and output movement data including information about the controller movements;
identifying an unintentional movement in the movement data with the processor, wherein the unintentional movement includes at least one of a jerked controller, a bobbled controller, or a shaken controller;
outputting unintentional movement data, wherein the unintentional movement data identifies one of the controller movements described by the movement data as being associated with the unintentional movement; and
sending the unintentional movement data to a surgical robot to enable the surgical robot to restrict robotic movement in response to the unintentional movement data.

13. The method of claim 12, further comprising:
receiving, with the processor, tactile data from the controller, wherein the tactile data is indicative of a user touching the controller, and wherein the unintentional movement is identified at least in part using the tactile data.

14. The method of claim 12, and wherein the tactile data is output from at least one of a button, a pressure sensor, or a capacitive sensor.

15. The method of claim 14, wherein the processor includes a machine learning algorithm disposed in logic, wherein the machine learning algorithm is used to identify the unintentional movement from the movement data and the tactile data.

16. The method of claim 15, wherein the machine learning algorithm includes at least one of recurrent neural network (RNN) or a long-short term memory (LSTM) network.

17. The method of claim 15, wherein the machine learning algorithm is used in conjunction with one or more heuristics in the logic to identify the unintentional movement.

18. The method of claim 12, wherein the movement data includes information about six degrees of freedom of the one or more controllers.

* * * * *